(12) United States Patent
Ryu et al.

(10) Patent No.: US 11,544,631 B2
(45) Date of Patent: Jan. 3, 2023

(54) BLOOD FLOW MEASUREMENT APPARATUS USING DOPPLER ULTRASOUND AND METHOD OF OPERATING THE SAME

(71) Applicant: HEALCERION CO., LTD., Seoul (KR)

(72) Inventors: Jeong Won Ryu, Seoul (KR); You Chan Choung, Seoul (KR)

(73) Assignee: HEALCERION CO., LTD., Gyeonggi-do (KR)

( * ) Notice: Subject to any disclaimer, the term of this patent is extended or adjusted under 35 U.S.C. 154(b) by 223 days.

(21) Appl. No.: 16/670,410

(22) Filed: Oct. 31, 2019

(65) Prior Publication Data
US 2020/0151612 A1 May 14, 2020

(30) Foreign Application Priority Data
Nov. 8, 2018 (KR) .......................... 10-2018-0136382

(51) Int. Cl.
*A61B 8/08* (2006.01)
*A61B 8/06* (2006.01)
*G06N 20/20* (2019.01)

(52) U.S. Cl.
CPC .............. *G06N 20/20* (2019.01); *A61B 8/065* (2013.01); *A61B 8/488* (2013.01); *A61B 8/5207* (2013.01)

(58) Field of Classification Search
None
See application file for complete search history.

(56) References Cited

U.S. PATENT DOCUMENTS

| | | | |
|---|---|---|---|
| 6,582,367 B1* | 6/2003 | Robinson | G01S 15/8925 600/443 |
| 2007/0016050 A1* | 1/2007 | Moehring | A61B 5/725 600/454 |
| 2011/0046484 A1* | 2/2011 | Adams | G10K 11/346 600/440 |
| 2017/0188993 A1* | 7/2017 | Hamilton | A61B 8/0808 |

\* cited by examiner

*Primary Examiner* — Amanda Lauritzen Moher
*Assistant Examiner* — Delia M. Appiah Mensah
(74) *Attorney, Agent, or Firm* — Harness, Dickey & Pierce, P.L.C.

(57) ABSTRACT

Disclosed is a blood flow measurement apparatus using Doppler ultrasound. The apparatus includes a two-dimensional transducer array in which a plurality of transducers are two-dimensionally arranged, an acoustic window detection portion configured to transmit and receive ultrasonic signals by driving some of the plurality of transducers, to detect Doppler signals, and to confirm a transducer corresponding to a Doppler signal having high intensity among the detected Doppler signals, a blood flow detection portion configured to detect Doppler signals with respect to a plurality of steering vectors through beam steering using a plurality of adjacent transducers including the confirmed transducer and configured to confirm a steering vector corresponding to a Doppler signal having highest intensity among the detected Doppler signals, and a Doppler processing portion configured to detect a Doppler signal by performing beam steering using the confirmed steering vector and to obtain blood flow information from the detected Doppler signal.

9 Claims, 8 Drawing Sheets

BLOOD FLOW MEASUREMENT APPARATUS USING DOPPLER ULTRASOUND AND METHOD OF OPERATING THE SAME

CROSS-REFERENCE TO RELATED APPLICATION

This application claims priority to and the benefit of Korean Patent Application No. 10-2018-0136382, filed on Nov. 8, 2018, the disclosure of which is incorporated herein by reference in its entirety.

FIELD

The present invention relates to an ultrasonic diagnosis, and more particularly, to a blood flow measurement apparatus using Doppler ultrasound and a method of operating the same.

BACKGROUND

Generally, measurement of a blood flow rate in a blood vessel is generally utilized to diagnose a disease. Ultrasonic diagnosis systems using Doppler effect are generally used.

A method of measuring a blood flow using Doppler effect of ultrasonic waves has a feature capable of noninvasively measuring a speed of a blood flow in real time and is generally utilized in diagnosis of modern medicine.

In an ultrasonic diagnosis system using Doppler effect, a speed of an object is determined by transmitting an ultrasonic signal to a target such as a red blood cell, receiving the signal reflected from the object, and then detecting frequency deviation of the received signal caused by movement of the object.

That is, an ultrasonic wave having a particular frequency is incident on a human body and the ultrasonic wave reflected by a red blood cell flowing through a blood vessel is detected. Here, since a frequency of the detected ultrasonic wave is different from the frequency of the incident ultrasonic wave, a blood flow rate is measured by detecting such variations of frequency.

In a brief description of a principle of measuring a blood flow rate using an ultrasonic signal, an ultrasonic signal is transmitted to a target through an ultrasonic probe and the ultrasonic signal reflected by the target is obtained through the ultrasonic probe.

Here, when the target moves, a center frequency of the reflected signal changes from a center frequency of the transmitted signal. A movement speed of the target may be calculated from variations of the center frequency of the reflected signal. Here, the movement speed of the target is proportional to Doppler shift of the signal reflected by the target.

In the case of a patient of a cardiovascular disease such as a stroke and the like, it is necessary to monitor a state of a disease by measuring a blood flow rate of a blood vessel. To this end, the blood flow rate is measured using Doppler ultrasound. For example, a transcranial Doppler (TCD) ultrasonography is a method of measuring a blood flow rate and Doppler spectrum waveforms in a blood vessel in a cranial cavity using ultrasonic waves of a low frequency of 2 MHz. In TCD, an ultrasonic wave is launched into a cranium, an echo reflected by a red blood cell of a blood vessel is analyzed, and Doppler shift is converted into a velocity and shown as Doppler spectrum.

However, since it is generally difficult for an ultrasonic signal to pass through a cranium, it is necessary to measure a blood flow through an acoustic window which is a thin part of the cranium (for example, a vicinity of a temple of temporal lobe) in TCD. Since the acoustic window is a relatively thin part of the cranium through which an ultrasonic signal easily passes anatomically and includes a temporal window, an orbital window, a suboccipital window, a submandibula window, a retromandibular window, and the like.

However, since the acoustic window has a narrow area and an anatomical position slightly differs for each person and is not seen with naked eyes, it is necessary to detect the position depending on user's experiences and generally accompanies trial and error. Also, even when an ultrasonic probe is located in the acoustic window, in order to obtain a precise Doppler signal, it is necessary that a user who anatomically well understands a direction in which a blood vessel is present and allows a direction of the ultrasonic probe to face the direction in which the blood vessel is present.

Accordingly, blood flow measurement of TCD and the like can be performed by only skilled experts and it is necessary to perform correction in real time according to movement or posture of a patient such that a lot of time and efforts are necessary for measurement.

SUMMARY

The present invention is directed to providing a blood flow measurement apparatus using Doppler ultrasound which is capable of significantly reducing time and efforts for detecting an acoustic window and a blood vessel direction while measuring a blood flow using Doppler ultrasound, and a method of operating the blood flow measurement apparatus.

Aspects of the present invention are not limited to the above-stated aspect and other unstated aspects of the present invention will be understood by those skilled in the art from a following description.

According to an aspect of the present invention, there is provided a blood flow measurement apparatus using Doppler ultrasound. The apparatus includes a two-dimensional transducer array in which a plurality of transducers configured to transmit and receive ultrasonic signals with an object are two-dimensionally arranged, an acoustic window detection portion configured to transmit and receive ultrasonic signals by driving some of the plurality of transducers, to detect Doppler signals with respect to the some transducers, and to confirm a transducer corresponding to a Doppler signal having high intensity among the detected Doppler signals, a blood flow detection portion configured to detect Doppler signals with respect to a plurality of steering vectors through beam steering using a plurality of adjacent transducers including the confirmed transducer and configured to confirm a steering vector corresponding to a Doppler signal having highest intensity among the detected Doppler signals, and a Doppler processing portion configured to detect a Doppler signal by performing beam steering using the confirmed steering vector and to obtain blood flow information from the detected Doppler signal.

The acoustic window detection portion may drive the some transducers at the same time.

The blood flow measurement apparatus may further include a multiplexer connected to the two-dimensional transducer array so as to drive the some transducers at the same time.

The some transducers may be distributed to be scattered in the two-dimensional transducer array.

An ultrasonic signal transmitted from each of the some transducers may be a spherical wave signal.

The number of the some transducers may be an available channel number or less.

The blood flow detection portion may confirm two or more steering vectors corresponding to a Doppler signal greater than a certain threshold value among the detected Doppler signals.

The acoustic window detection portion may confirm a transducer corresponding to the Doppler signal having highest intensity through machine learning.

According to another aspect of the present invention, there is provided a method of operating a blood flow measurement apparatus using Doppler ultrasound. The method includes (a) transmitting and receiving ultrasonic signals by driving some transducers of a two-dimensional transducer array in which a plurality of transducers configured to transmit and receive ultrasonic signals with an object are two-dimensionally arranged, and detecting Doppler signals with respect to the some transducers, (b) confirm a transducer corresponding to a Doppler signal having highest intensity among the detected Doppler signals, (c) detecting Doppler signals with respect to the plurality of steering vectors through beam steering using a plurality of adjacent transducers including the confirmed transducer, (d) confirm a steering vector corresponding to a Doppler signal having highest intensity among the detected Doppler signals, and (e) detecting a Doppler signal by performing beam steering using the confirmed steering vector and obtaining blood flow information from the detected Doppler signal.

The some transducers may be driven at the same time.

The some transducers may be distributed to be scattered in the two-dimensional transducer array.

An ultrasonic signal transmitted from each of the some transducers may be a spherical wave signal.

The number of the some transducers may be an available channel number or less.

The operation (d) may include confirming two or more steering vectors corresponding to a Doppler signal greater than a certain threshold value among the detected Doppler signals.

The operation (b) may include confirming a transducer corresponding to the Doppler signal having highest intensity through machine learning.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

Figure 1:
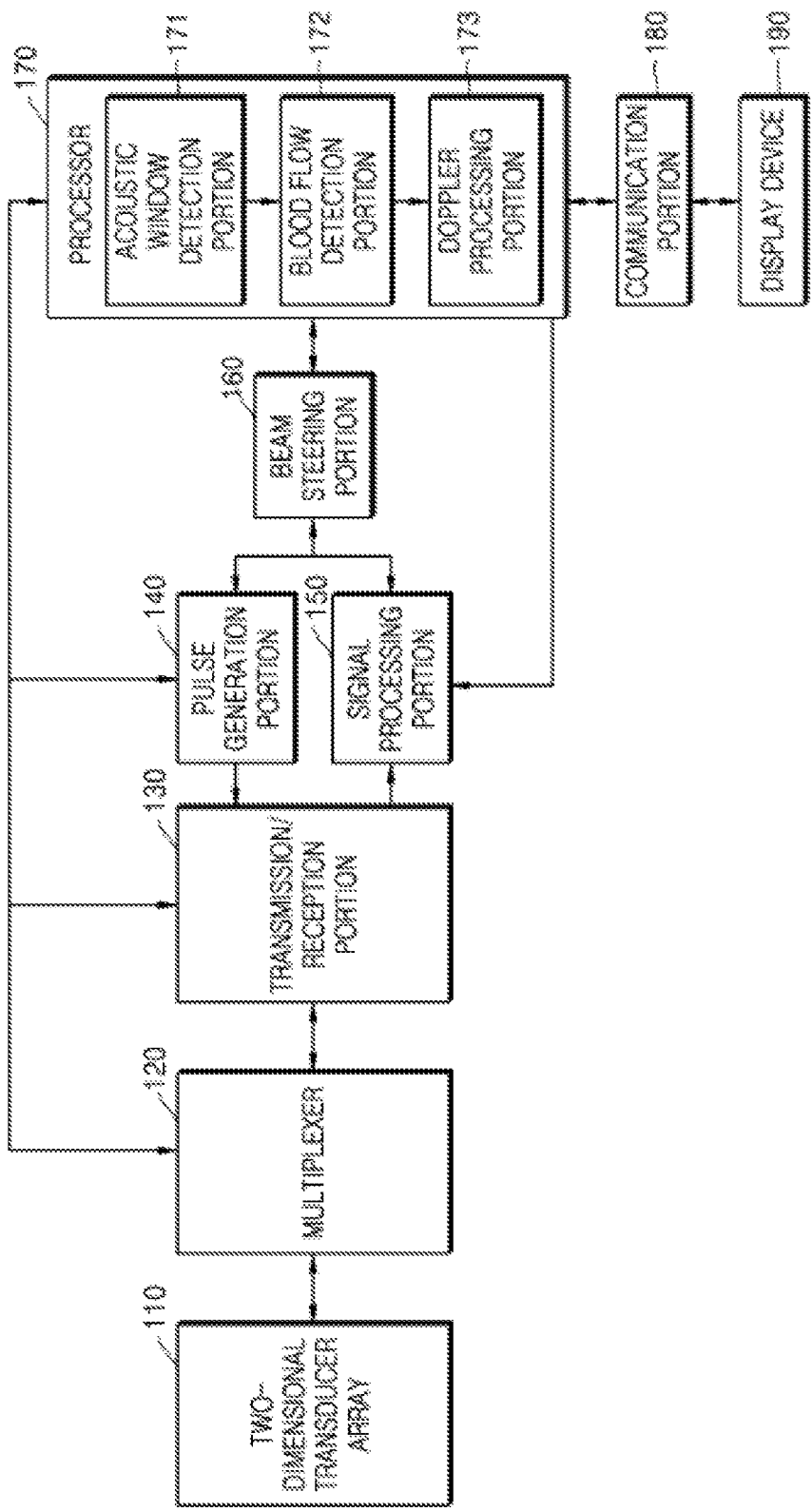
FIG. 1 illustrates a configuration of a blood flow measurement apparatus using Doppler ultrasound according to one embodiment of the present invention.

Hereinafter, exemplary embodiments of the present invention will be described in detail with reference to the drawings. Hereinafter, in the description and the attached drawings, substantially like elements will be referred to as with like reference numerals and a repetitive description thereof will be omitted. Also, in a description of embodiments of the present invention, a detailed description of a well-known technology of the related art will be omitted when it is deemed to obscure the essence of the present invention.

FIG. 1 illustrates a configuration of a blood flow measurement apparatus using Doppler ultrasound according to one embodiment of the present invention.

Referring to FIG. 1, the blood flow measurement apparatus using Doppler ultrasound according to the embodiment may include a two-dimensional transducer array 110, a multiplexer 120, a transmission/reception portion 130, a pulse generation portion 140, a signal processing portion 150, a beam steering portion 160, a processor 170, a communication portion 180, and a display device 190.

The two-dimensional transducer array 110 is formed by two-dimensionally arranging a plurality of transducers configured to transmit and receive ultrasonic signals. Each of the plurality of transducers included in the two-dimensional transducer array 110 may convert an input electrical signal into an ultrasonic signal, transmit the ultrasonic signal to an object, receive the ultrasonic signal reflected from the object, and convert the received ultrasonic signal into an electrical signal.

The multiplexer 120 is configured to drive transducers of a channel number (or less) supported by a device among the transducers of the two-dimensional transducer array 110, selects transducers to be driven, and matches signal line numbers of the two-dimensional transducer array 110 and a rear end of the multiplexer 120. That is, in order to drive some transducers of the two-dimensional transducer array 110 when an ultrasonic signal is transmitted or an echo signal is received, the multiplexer 120 connects the corresponding transducers to the transmission/reception portion 130.

The transmission/reception portion 130, under the control of the processor 170, transmits a high voltage pulse signal generated by the pulse generation portion 140 to the two-dimensional transducer array 110 through the multiplexer 120 or transmits an analog echo signal received from the two-dimensional transducer array 110 through the multiplexer 120 to the signal processing portion 150. In detail, the transmission/reception portion 130 performs a switching operation of connecting a TX circuit formed of the processor 170, the beam steering portion 160, and the pulse generation portion 140 to the two-dimensional transducer array 110 when transmitting an ultrasonic signal and performs a switching operation of connecting the two-dimensional transducer array 110 to an RX circuit formed of the signal processing portion 150, the beam steering portion 160, and the processor 170.

The pulse generation portion 140 generates a high voltage pulse signal to be applied to the two-dimensional transducer array 110 (precisely, some transducers of the two-dimensional transducer array 110) to generate an ultrasonic signal. The pulse signal is, for example, 2 MHz and has a certain pulse repetition frequency (PRF). A delay time for determining transmission directionality may be applied to a pulse signal of each channel to be applied to each transducer.

The signal processing portion 150 generates ultrasonic data by processing an analog echo signal reflected and received from an object. The signal processing portion 150 may amplify the echo signal for each channel, remove noise therefrom, and perform analog-digital conversion. A delay time for determining reception directionality may be applied to the digital-converted echo signal.

The beam steering portion 160 performs beam steering to transmit an ultrasonic signal to an interested region of particular steering vectors (that is, a particular distance and a particular direction) and to receive an echo signal under the control of the processor 170. The beam steering portion 160 may apply a transmission delay time to the pulse generation portion 140 and apply a reception delay time to the signal processing portion 150 to perform beam steering.

The processor 170 may control operations of components forming the device, that is, the multiplexer 120, the transmission/reception portion 130, the pulse generation portion 140, the signal processing portion 150, the beam steering portion 160, the communication portion 180, and the like, detect a Doppler signal from ultrasonic data, obtain blood flow information such as a speed, a direction, and the like of a blood flow on the basis of the detected Doppler signal, and generate a Doppler image which shows the blood flow information with colors or waveforms. The Doppler image may include a blood flow Doppler image (otherwise, referred to as a color flow image) which indicates a flow of blood, a tissue Doppler image which indicates movement of tissue, a spectral Doppler image which indicates a movement speed of an object with waveforms, and the like.

The processor 170 may include an acoustic window detection portion 171, a blood flow detection portion 172, and a Doppler processing portion 173. Detailed movements thereof will be described in detail with reference to FIG. 2.

The communication portion 180 is configured to transmit or receive data with another device such as the display device 190 or the like and may transmit blood flow information of a Doppler image to the display device under the control of the processor 170. The communication portion 180 may use a wired or wireless communication method to perform data transmission. As the wired communication method, data may be transmitted or received using a wired cable such as a universal serial bus (USB) cable and the like. As the wireless communication method, Bluetooth, wireless USB, wireless local area network (LAN), WiFi, Zigbee, infrared data association (IrDA), and the like may be used.

The display device 190 receives and displays blood flow information or a Doppler image on a screen. The display device 190 may include a smart phone, a tablet personal computer (PC), a mobile phone, a video phone, an e-book reader, a desktop PC, a laptop PC, a netbook computer, a workstation, a personal digital assistant, a portable multimedia player (PMP), and the like.

Also, the communication portion 180 may be connected through a network through wires or wirelessly and communicate with an external device or server. The communication portion 180 may transmit or receive data with a server or other medical devices in a clinic which are connected through a picture archiving and communication system (PACS). Also, the communication portion 180 may communicate data according to digital imaging and communications in medicine (DICOM) standards. In addition, the communication portion 270 may perform data communication with not only the server or medical devices in the clinic but also a portable terminal of a physician, patient, or guardian.

Figure 2:
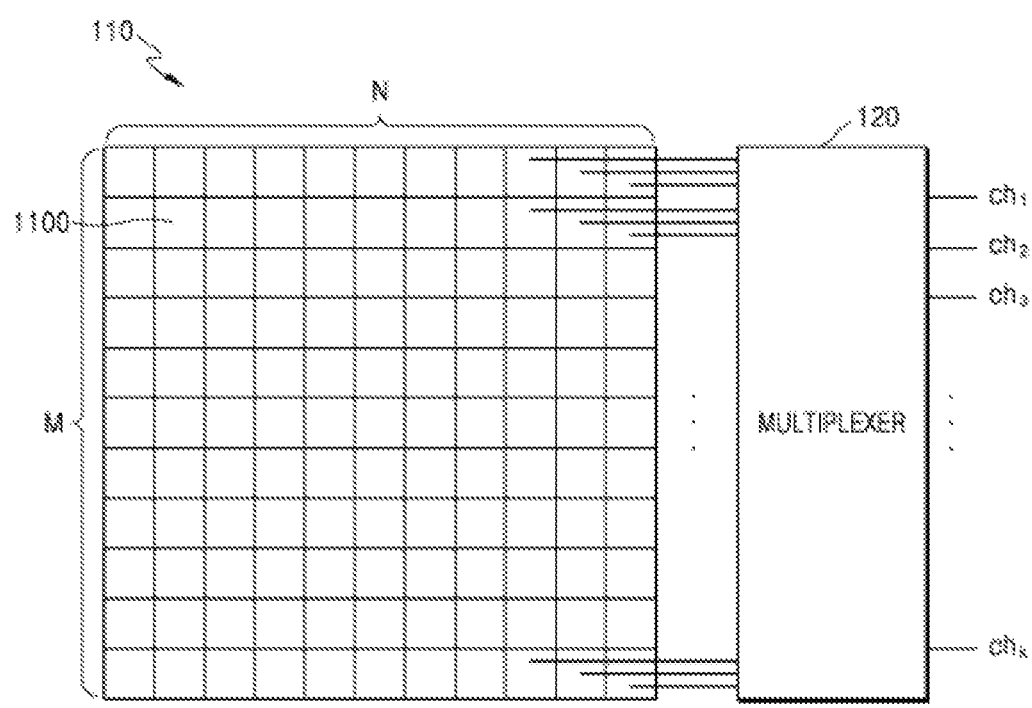
FIG. 2 illustrates an example of a two-dimensional transducer array.

FIG. 2 illustrates an example of the two-dimensional transducer array 110. For example, the two-dimensional transducer array 110 may include M×N number of transducers 1100 arranged in an M number of rows and an N number of columns as shown in the drawing. Here, M and N may be the same number or different numbers.

When the device supports a K number of channels, the multiplexer 120 may be connected to the transmission/reception portion 130 through a K number of signal lines and may be connected to the two-dimensional transducer array 110 through an M×N number of signal lines. The M×N number of signal lines correspond to the transducers 1100 included in the two-dimensional transducer array 110. The multiplexer 120 may drive the required K number (or less) of transducers by performing a switching operation of connecting signals lines corresponding to the transducers to be driven among the M×N number of signal lines to the K number of signal lines under the control of the processor 170.

The acoustic window detection portion 171 transmits and receives an ultrasonic signal by driving some of the transducers of the two-dimensional transducer array 110 at the same time and detects Doppler signals with respect to the driven some transducers. Here, the ultrasonic signal transmitted by each of the driven transducers becomes a spherical wave which has no or less directivity. Also, the acoustic window detection portion 171 confirms a transducer corresponding to a Doppler signal having highest intensity among the detected Doppler signals and regards the transducer as a transducer located in an acoustic window.

Figure 3:
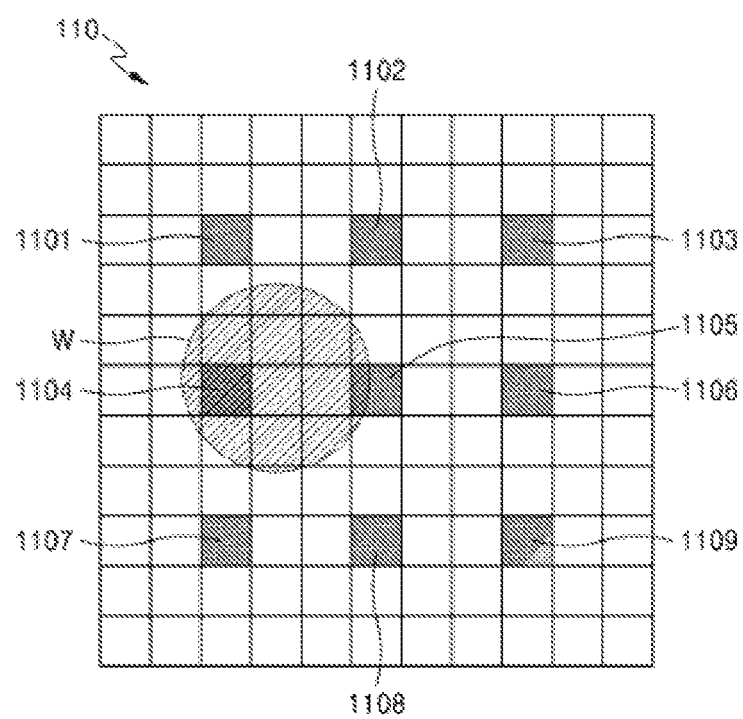
FIG. 3 illustrates an acoustic window of an object in which some of driven transducers and a two-dimensional transducer array are arranged.
Figure 4:
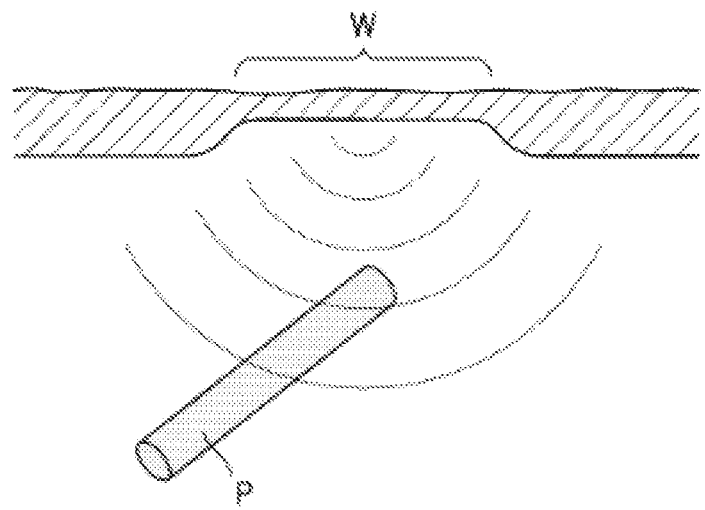
FIG. 4 schematically illustrates a cross section of an acoustic window part of cranium.

FIG. 3 illustrates an acoustic window of an object in which some transducers driven by the acoustic window detection portion 171 and the two-dimensional transducer array 110 are arranged, and FIG. 4 schematically illustrates a cross section of an acoustic window part of cranium.

Referring to FIG. 4, an ultrasonic signal is practically reflected by a thick bone part of most of cranium and does not reach to a depth thereinside. However, the ultrasonic signal may pass through an acoustic window W region which is a thin part in comparison to a periphery thereof like a vicinity of temple of temporal lobe at which a thin bone is placed and reach a blood vessel P.

The acoustic window detection portion 171 may select transducers to be driven to be distributed and scattered to be relatively uniform within an available channel number among the transducers of the two-dimensional transducer array 110. FIG. 3 illustrates, for example, a case in which nine transducers 1101, 1102, . . . , and 1109 corresponding to nine channels are selected.

In the example of FIG. 3, as shown in the drawing, the acoustic window (actually not seen) is located over the transducer 1104 and the transducer 1105, and the transducer 1104 overlaps with a more part of the acoustic window W.

Since ultrasonic signals transmitted by the transducers 1104 and 1105 pass through the acoustic window W, when the ultrasonic signal is reflected by a blood flow of a blood vessel, a Doppler image may be detected. Here, since the transmitted ultrasonic signal has no or less directivity, even when the blood vessel does not pass just below the acoustic window W, a Doppler signal may be detected. However, since ultrasonic signals transmitted from the transducers 1101, 1102, 1103, 1106, 1107, 1108, and 1109 do not pass through the acoustic window W and do not reach the blood flow of the blood vessel, Doppler images are not detected.

Figure 5:
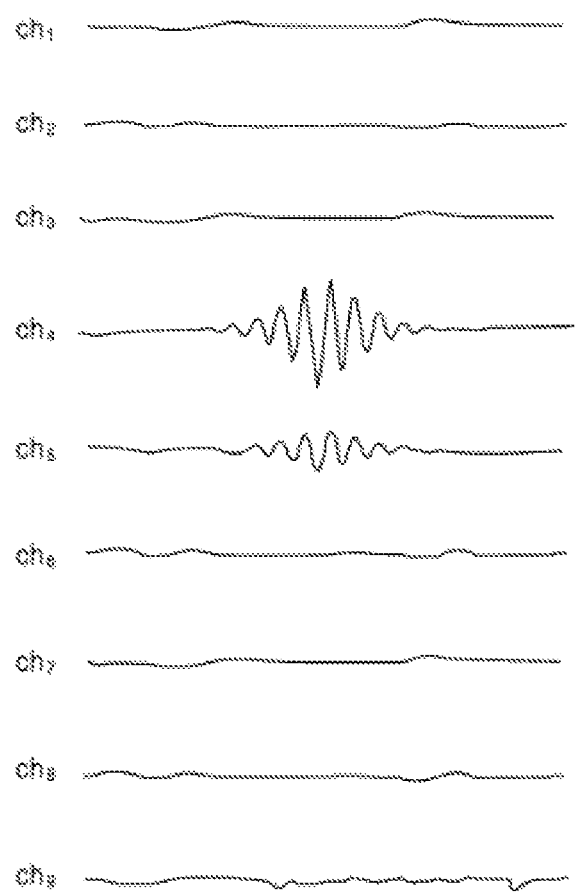
FIG. 5 illustrates an example of a Doppler signal detected with respect to each of some of driven transducers.

FIG. 5 illustrates Doppler images detected with respect to nine channels, that is, the nine transducers 1101, 1102, ..., and 1109. Referring to FIG. 5, a Doppler signal having highest intensity is detected from a fourth channel, and a Doppler signal having intensity lower than that of the fourth channel is detected from a fifth channel. This is because the transducer 1104 corresponding to the fourth channel overlaps with a larger part of the acoustic window W than that of the transducer 1105 corresponding to the fifth channel.

Accordingly, the acoustic window detection portion 171 regards the transducer 1104 of the fourth channel corresponding to the Doppler signal having the highest intensity as a transducer located in the acoustic window W.

The acoustic window detection portion 171 may detect a position of an acoustic window at once through the above operation and may detect an optimum acoustic window through a plurality of times by changing transducers to be driven as necessary. For example, when a threshold value of the intensity of a Doppler signal is determined and all of detected Doppler signals are smaller than the threshold value, transducers are changed (for example, are shifted or selected again except the already selected) to transmit and receive ultrasonic signals such that a transducer from which a Doppler signal greater than the threshold is detected may be detected.

Meanwhile, since a Doppler signal generally has a poor signal-to-noise ratio and an ultrasonic signal from a single transducer is relatively insignificant, for example, a machine-learning algorithm such as a convolutional neural network and the like may be used in order to an optimal acoustic window. For example, patterns of Doppler signals as shown in FIG. 5 may be obtained from a plurality of patient samples whose positions of acoustic windows are known, and the transducer corresponding to the Doppler signal having highest intensity may be confirmed using the data through machine learning.

When a position of an acoustic window (that is, a transducer above the acoustic window) is confirmed by the acoustic window detection portion 171, the blood flow detection portion 172 detect Doppler signals with respect to a plurality of steering vectors through beam steering using a plurality of adjacent transducers including the corresponding transducer. Also, the blood flow detection portion 172 confirms a steering vector corresponding to the Doppler signal having the highest intensity among the detected Doppler signals, as a steering vector of a point where a blood flow of a blood vessel passes.

Figure 6:
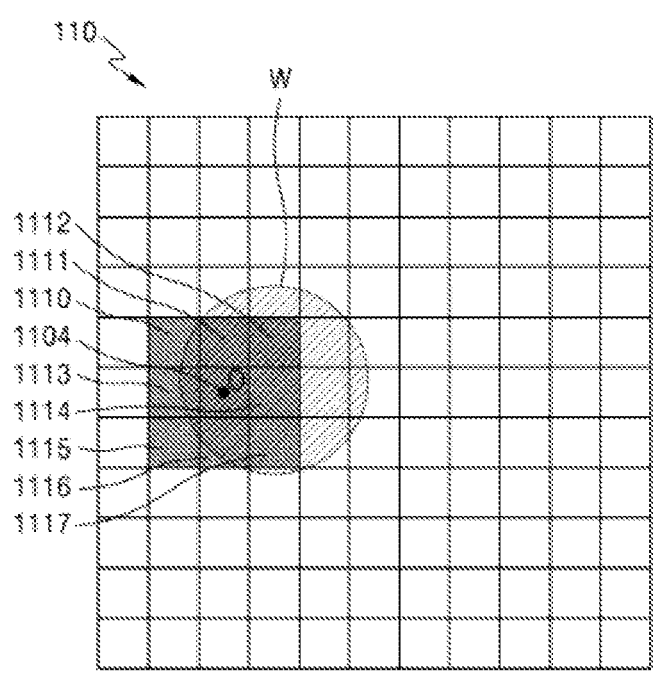
FIG. 6 illustrates an example of transducers selected to be driven for beam steering on an acoustic window.

FIG. 6 illustrates a case in which as the transducer 1104 among the nine transducers 1101, 1102, ..., and 1109 of FIG. 3 is confirmed as the transducer located above the acoustic window W, the adjacent transducers 1104, 1110, 1111, ..., and 1117 including the transducer 1104 are selected as transducers to be driven for beam steering. Although a central point of the transducer 1104 becomes a central point O of beam steering (that is, steering vector) in an example of FIG. 6, a particular point between the transducers may become the central point depending on arrangement or a shape of the transducer (for example, a variety of shapes such as a triangle, a hexagonal shape, and the like).

Figure 7:
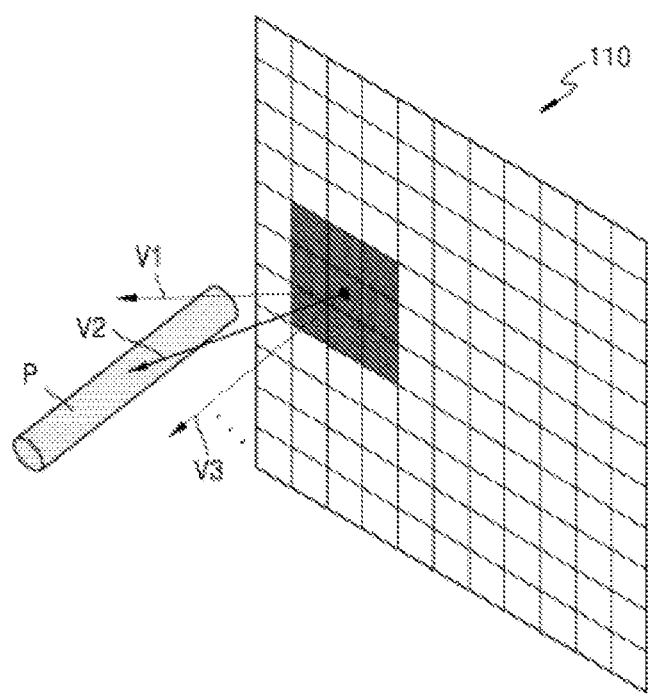
FIG. 7 illustrates an example of several steering vectors obtained through bema steering and a steering vector among them which heads for a blood flow spot in a blood vessel in an object.

FIG. 7 illustrates several steering vectors V1, V2, V3, ... obtainable through beam steering using the transducers 1104, 1110, 1111, ..., and 1117 of FIG. 6 and a blood vessel P in an object. For example, in the case of transcranial color Doppler (TCD), the blood vessel may be one of a middle cerebral artery, an anterior cerebral artery, a posterior cerebral artery, an ophthalmic artery, a vertebral artery, a basilar artery, and the like. Referring to FIG. 7, since a steering vector V2 is a steering vector of a point where a blood flow in the blood vessel P passes, a Doppler signal having highest intensity is detected from the steering vector V2.

Accordingly, the blood flow detection portion 172 confirms the steering vector V2 from which the Doppler signal having the highest intensity is detected, as a steering vector of a point where the blood flow in the blood vessel P passes.

When the steering vector of the point where the blood flow in the blood vessel passes is confirmed by the blood flow detection portion 172, the Doppler processing portion 173 performs beam steering using the corresponding steering vector and transmits and receives an ultrasonic signal using the corresponding steering vector to detect a Doppler signal. Also, the Doppler processing portion 173 may obtain blood flow information such as a speed, direction, and the like of the blood flow from the detected Doppler signal and generate a Doppler image shown as colors or waveforms.

The above blood flow detection operation of the blood flow detection portion 172 is not stopped and repetitively and continuously performed so as to track the blood flow in real time. Accordingly, when the steering vector corresponding to the Doppler signal having the highest intensity, that is, the steering vector of the point where the blood flow passes is changed, the Doppler processing portion 173 may detect a Doppler signal by performing beam steering using the changed steering vector.

Also, although the blood flow detection portion 172 may detect one steering vector corresponding to the Doppler signal having the highest intensity as described above, two blood vessels may be present. Accordingly, a thread value of Doppler signal intensity may be determined and two or more steering vectors corresponding to the Doppler signal greater than the threshold value may be detected such that blood flows of two or more blood vessels may be detected. In this case, the Doppler processing portion 173 may obtain blood flow information of two or more blood vessels by transmitting and receiving ultrasonic signals using respective steering vectors.

A part of the blood flow measurement apparatus using the Doppler ultrasound according to the embodiment of the present invention may be manufactured as a patch type and be attached to a measurement part of a patient. For example, the patch to be attached to the measurement part of the patient may include the two-dimensional transducer array 110, the multiplexer 120, the transmission/reception portion 130, the pulse generation portion 140, the signal processing portion 150, and the beam steering portion 160. Also, an addition set-top box connected to the patch through wires or wirelessly may include the processor 170, the communication portion 180, and the like. The display device 190 may be integrally included in the set-top box, and an external device such as a smart phone may be used as the display device 190.

Figure 8:
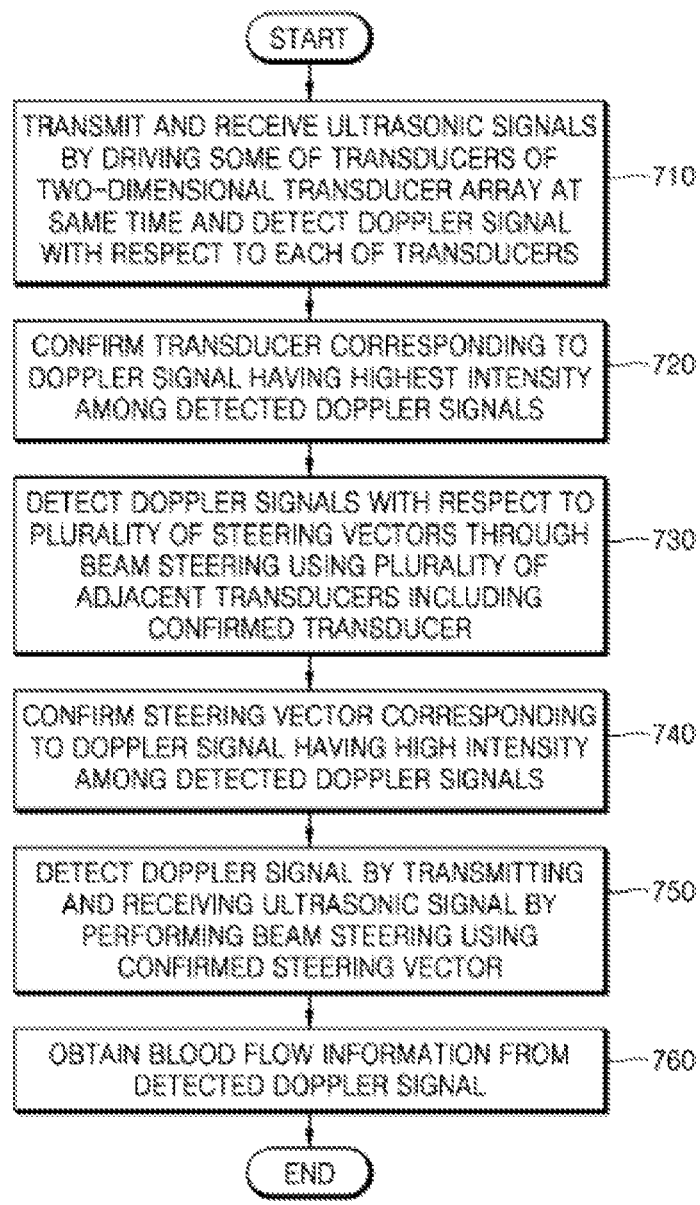
FIG. 8 is a flowchart illustrating a method of operating a blood flow measurement apparatus using Doppler ultrasound according to one embodiment of the present invention.

FIG. 8 is a flowchart illustrating a method of operating a blood flow measurement apparatus using Doppler ultrasound according to one embodiment of the present invention. Since the operation method according to the embodiment includes operations performed by the above-described blood flow measurement apparatus using Doppler ultrasound, the above description related to the blood flow measurement apparatus using Doppler ultrasound is applied to the operation method according to the embodiment even when a part of the description is omitted below.

In operation 710, an ultrasonic signal is transmitted and received by driving some of the transducers of the two-dimensional transducer array 110 at the same time and Doppler signals are detected with respect to the driven some transducers.

In operation 720, a transducer corresponding to a Doppler signal having highest intensity among the detected Doppler signals is confirmed.

In operation 730, Doppler signals with respect to a plurality of steering vectors are detected through beam steering using a plurality of adjacent transducers including the confirmed transducer.

In operation 740, a steering vector corresponding to the Doppler signal having highest intensity among the detected Doppler signals is confirmed.

In operation 750, beam steering is performed using the confirmed steering vector and a Doppler signal is detected by transmitting and receiving an ultrasonic signal using the corresponding steering vector so as to detect the Doppler signal.

In operation 760, blood flow information such as a speed, direction, and the like of a blood flow is obtained from the detected Doppler signal.

Embodiments of the present invention may be shown as functional block components and a variety of processing operations. The functional blocks may be implemented through a variety of numbers of hardware and/or software components which implement particular functions. For example, an embodiment may employ integrated circuit components such as a memory, processing, logic, look-up table, and the like which are capable of performing a variety functions under the control of one or more microprocessors or other control devices. Similar to the components of the present invention being executable using software programming or software elements, the embodiment may include a variety of algorithms which are implemented through a data structure, processes, routines, or a combination of other programming components and may be implemented as a programming or scripting language such as C, C++, Java, an assembler, and the like. Functional aspects may be implemented as an algorithm executed by one or more processors. Also, the embodiment may employ a related art for electronic environment settings, signal processing, data processing, and/or the like. The terms such as "mechanism," "element," "means," and "component" may be widely used and are not limited to mechanical and physical components. The terms may include the meaning of a series of routines of software in connection with a process and the like.

Particular executions described in the embodiment are merely examples, and the scope of the embodiment is not limited to any methods. For briefness of the specification, a description of conventional electronic components, control systems, software, and other functional aspects of the systems will be omitted. Also, connection or connection members of lines between components shown in the drawings are exemplarily shown as functional connection and/or physical or circuit connections and may be a variety of replaceable or additional functional connections, physical connection, or circuit connections in a real apparatus. Also, unless stated in detail such as "essential," "significant," and the like, a component may not be positively necessary for applying of the present invention.

According to the embodiments of the present invention, there is present an effect capable of significantly reducing time and efforts for detecting an acoustic window and a blood vessel direction while measuring a blood flow rate using Doppler ultrasound.

Although exemplary embodiments of the present invention have been described above, it will be understood by one of ordinary skill in the art that modifications of the present invention may be made without departing from the essential features of the present invention. Therefore, the disclosed embodiments should be considered not in a limited view but in a descriptive view. The scope of the present invention will be shown in the claims not in the above description, and all differences within an equivalent range thereof should be interpreted as being included in the present invention.

What is claimed is:

1. A blood flow measurement apparatus using Doppler ultrasound, comprising:
a two-dimensional transducer array in which a plurality of transducers are configured to transmit and receive ultrasonic signals with an object;
an acoustic window detection portion configured to transmit and receive ultrasonic signals by driving multiple transducers the plurality of transducers, to detect Doppler signals with respect to the multiple driven transducers based on the acoustic window overlapping with at least one of the multiple driven transducers, and to confirm a transducer corresponding to a Doppler signal having a highest intensity among the detected Doppler signals;
a blood flow detection portion configured to detect Doppler signals with respect to a plurality of steering vectors through beam steering using a plurality of adjacent transducers including the confirmed transducer and configured to confirm a steering vector corresponding to a Doppler signal having a highest intensity among the detected Doppler signals; and
a Doppler processing portion configured to detect a Doppler signal by performing beam steering using the confirmed steering vector and to obtain blood flow information from the detected Doppler signal, wherein the multiple driven transducers based on the acoustic window overlapping with at least one of the multiple driven transducers are selected by the acoustic window detection portion to be scattered in the two-dimensional transducer array,
wherein at least one non-driven transducer of the plurality of transducers is between the multiple driven transducers of the plurality of transducers in the two-dimensional transducer, and wherein the acoustic window detection portion drives all of the multiple transducers selected by the acoustic window detection portion at the same time.

2. The blood flow measurement apparatus of claim 1, further comprising a multiplexer connected to the two-dimensional transducer array.

3. The blood flow measurement apparatus of claim 1, wherein an ultrasonic signal transmitted from each of the multiple transducers is a spherical wave signal.

4. The blood flow measurement apparatus of claim 1, wherein the number of the multiple transducers is an available channel number or less.

5. The blood flow measurement apparatus of claim 1, wherein the blood flow detection portion confirms two or more steering vectors corresponding to a Doppler signal greater than a certain threshold value among the detected Doppler signals.

6. A method of operating a blood flow measurement apparatus using Doppler ultrasound, the method comprising:
- (a) transmitting and receiving ultrasonic signals by driving multiple transducers of a plurality of transducers arranged in a two-dimensional transducer array, the plurality of transducers configured to transmit and receive ultrasonic signals with an object, and detecting Doppler signals with respect to the multiple driven transducers based on the acoustic window overlapping with at least one of the multiple driven transducers;
- (b) confirming a transducer corresponding to a Doppler signal having a highest intensity among the detected Doppler signals;
- (c) detecting Doppler signals with respect to a plurality of steering vectors through beam steering using a plurality of adjacent transducers including the confirmed transducer;
- (d) confirming a steering vector corresponding to a Doppler signal having a highest intensity among the detected Doppler signals; and
- (e) detecting a Doppler signal by performing beam steering using the confirmed steering vector and obtaining blood flow information from the detected Doppler signal, wherein the multiple driven transducers are selected by an acoustic window detection portion to be scattered in the two-dimensional transducer array, wherein at least one non-driven transducer of the plurality of transducers is between the multiple driven transducers of the plurality of transducers in the two-dimensional transducer, and wherein all of the multiple transducers selected by the acoustic window detection portion are driven at the same time.

7. The method of claim 6, wherein an ultrasonic signal transmitted from each of the multiple transducers is a spherical wave signal.

8. The method of claim 6, wherein the number of the multiple transducers is an available channel number or less.

9. The method of claim 6, wherein the operation (d) comprises confirming two or more steering vectors corresponding to a Doppler signal greater than a certain threshold value among the detected Doppler signals.

* * * * *